United States Patent
Wang et al.

(10) Patent No.: US 9,778,219 B2
(45) Date of Patent: Oct. 3, 2017

(54) ELECTROCHEMICAL DETECTION SYSTEM AND METHOD OF OPERATION

(71) Applicant: DELPHI TECHNOLOGIES, INC., Troy, MI (US)

(72) Inventors: Da Yu Wang, Troy, MI (US); David M. Racine, Grand Blanc, MI (US); Sheng Yao, Macomb, MI (US)

(73) Assignee: DELPHI TECHNOLOGIES, INC., Troy, MI (US)

( * ) Notice: Subject to any disclaimer, the term of this patent is extended or adjusted under 35 U.S.C. 154(b) by 810 days.

(21) Appl. No.: 14/091,498

(22) Filed: Nov. 27, 2013

(65) Prior Publication Data
US 2015/0144504 A1    May 28, 2015

(51) Int. Cl.
G01N 27/30    (2006.01)
G01N 27/416   (2006.01)
G01M 15/10    (2006.01)

(52) U.S. Cl.
CPC ....... *G01N 27/301* (2013.01); *G01N 27/4162* (2013.01); *G01M 15/102* (2013.01)

(58) Field of Classification Search
CPC ............. G01N 27/301; G01N 27/3274; G01N 27/4162; G01M 15/102
See application file for complete search history.

(56) References Cited

U.S. PATENT DOCUMENTS

| | | | |
|---|---|---|---|
| 5,323,320 A | * | 6/1994 | Hathaway ............. F16H 61/143 192/3.3 |
| 7,074,319 B2 | | 7/2006 | Wang et al. |
| 7,294,252 B2 | | 11/2007 | Wang et al. |
| 7,722,749 B2 | | 5/2010 | Wang et al. |
| 7,828,955 B2 | | 11/2010 | Wang et al. |
| 7,975,537 B2 | | 7/2011 | Wang et al. |
| 2003/0235817 A1 | | 12/2003 | Bartkowiak et al. |
| 2005/0230248 A1 | * | 10/2005 | Kawase ............. G01N 27/4175 204/424 |
| 2011/0023459 A1 | * | 2/2011 | Nieuwstadt ........... F02D 41/064 60/285 |
| 2012/0309324 A1 | * | 12/2012 | Rudd ...................... G01S 15/36 455/67.16 |

* cited by examiner

Primary Examiner — Susan D Leong
(74) Attorney, Agent, or Firm — Joshua M. Haines

(57) ABSTRACT

An electrochemical detection system for determining a concentration of a gas in exhaust gases of a combustion process. The system includes an electrolyte, a reference electrode, and a sense electrode that cooperate to form an electrochemical sensor that exposes both the reference electrode and the sense electrode to the exhaust gases. The electrochemical sensor is configured to output a sensor signal indicative of a species concentration of a species gas in the exhaust gases. The sensor signal exhibits a transient error in response to a change in a reference concentration of a reference gas in the exhaust gases. The processor is configured to determine the species concentration based on the sensor signal, and to determine an estimate of the transient error based on an operating condition of the combustion process.

6 Claims, 4 Drawing Sheets

ELECTROCHEMICAL DETECTION SYSTEM AND METHOD OF OPERATION

TECHNICAL FIELD OF INVENTION

This disclosure generally relates to an electrochemical detection system, and more particularly relates to a way to compensate for error signals caused by transient changes in the concentration of a reference gas detected by an electrochemical sensor.

BACKGROUND OF INVENTION

Electrochemical sensors that use two electrodes (e.g. a reference electrode and a sense electrode) attached to an electrolyte to determine the concentration of a particular species of gas are known. An electrochemical sensor can be made sensitive to a particular species gas by forming the electrodes using different material and/or different processes. Such electrochemical sensors can be used to discern the species concentration in a mixture of gases by exposing both electrodes to the mixture. Relevant examples of such electrochemical sensors are described in commonly owned U.S. Pat. Nos. 7,074,319; 7,722,749; 7,828,955; and 7,975,537, all issued to Wang et al. However, it has been observed that if the concentration of a certain reference gas in the mixture suddenly changes (i.e. a change in the reference concentration), there may be a transient error in the sensor signal output by the electrochemical sensor that could be misinterpreted as a change in the species concentration.

SUMMARY OF THE INVENTION

In accordance with one embodiment, an electrochemical detection system configured to determine a concentration of a gas in exhaust gases of a combustion process is provided. The system includes an electrolyte, a reference electrode, a sense electrode, and a processor. The reference electrode is in contact with the electrolyte. The sense electrode is in contact with the electrolyte and spaced apart from the reference electrode. The electrolyte, the reference electrode, and the sense electrode cooperate to form an electrochemical sensor that exposes both the reference electrode and the sense electrode to the exhaust gases. The electrochemical sensor is configured to output a sensor signal indicative of a species concentration of a species gas in the exhaust gases. The sensor signal exhibits a transient error in response to a change in a reference concentration of a reference gas in the exhaust gases. The processor is configured to determine the species concentration based on the sensor signal, and to determine an estimate of the transient error based on an operating condition of the combustion process.

In another embodiment, a controller configured to determine a concentration of a gas in exhaust gases of a combustion process based on a sensor signal from an electrochemical sensor is provided. The electrochemical sensor is configured to expose both a reference electrode and a sense electrode of the electrochemical sensor to the exhaust gases. The sensor signal is indicative of a species concentration of a species gas in the exhaust gases. The sensor signal exhibits a transient error in response to a change in a reference concentration of a reference gas in the exhaust gases. The controller includes a processor configured to determine the species concentration based on the sensor signal, and to determine an estimate of the transient error based on an operating condition of the combustion process.

In yet another embodiment, a method to determine a concentration of a gas in exhaust gases of a combustion process is provided. The method includes receiving a sensor signal from an electrochemical sensor. The electrochemical sensor is configured to expose both a reference electrode and a sense electrode of the electrochemical sensor to the exhaust gases. The sensor signal is indicative of a species concentration of a species gas in the exhaust gases. The sensor signal exhibits a transient error in response to a change in a reference concentration of a reference gas in the exhaust gases. The method also includes determining the species concentration based on the sensor signal. The method also includes estimating the transient error based on an operating condition of the combustion process.

Further features and advantages will appear more clearly on a reading of the following detailed description of the preferred embodiment, which is given by way of non-limiting example only and with reference to the accompanying drawings.

BRIEF DESCRIPTION OF DRAWINGS

The present invention will now be described, by way of example with reference to the accompanying drawings, in which.

DETAILED DESCRIPTION

Figure 1:
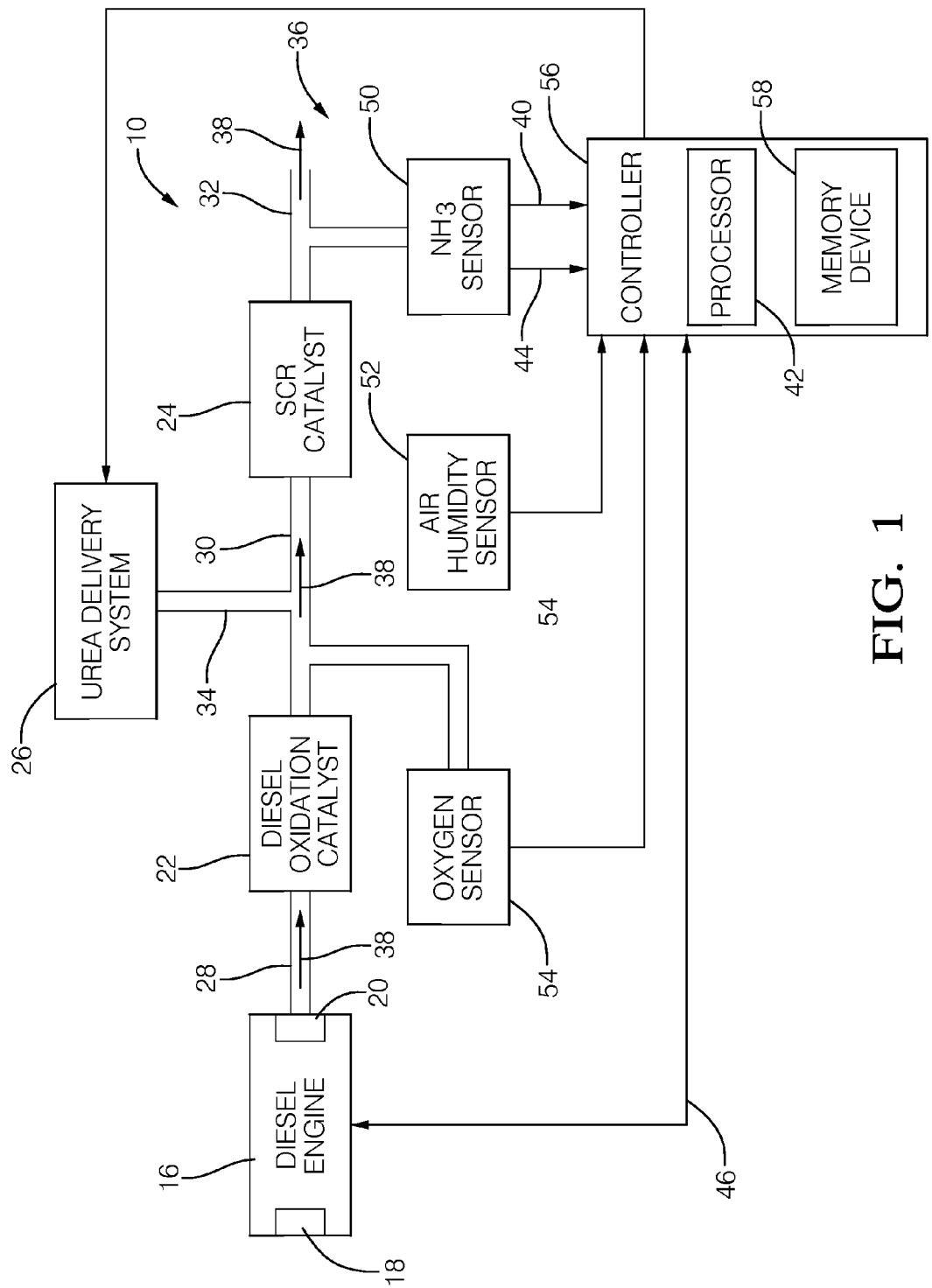
FIG. 1 is a block diagram of a system for determining a concentration of a gas in exhaust gases of a combustion process in accordance with one embodiment.

FIG. 1 illustrates a non-limiting example of a vehicle 10, that may include a diesel engine 16, a diesel oxidation catalyst 22, a selective catalytic reduction (SCR) catalyst 24, a urea delivery system 26, exhaust pipes 28, 30, 32, a urea-water spray tube 34, and a control system, hereafter referred to as the system 36. An advantage of the system 36 in this non-limiting example is that the system 36 can determine a species concentration of a species gas (e.g. ammonia ($NH_3$) concentration) in exhaust gases 38 emitted by the diesel engine 16 even if excess water and oxygen is present in the exhaust gases 38. While this non-limiting example shows an internal combustion engine as the source of the exhaust gases 38, it is contemplated that the teachings presented herein could be applied to any controlled combustion process that includes controls able to actively vary the mixture of gases that make up the exhaust gases. Examples of such controlled combustion processes are found in industrial reactors, burners, furnaces, or ovens. It is also contemplated that the system 36 may be configured to detect the species concentration of some other species of gas other than $NH_3$ in exhaust from a diesel or gasoline internal combustion, or other combustion processes.

The diesel engine 16 receives air in an air intake manifold 18 and combusts an air-fuel mixture therein. The amount of fuel delivered to the combustion process is generally controlled via the engine control signal 46. Thereafter, the diesel engine 16 routes exhaust gases from an exhaust manifold 20 through the exhaust pipe 28 to the diesel oxidation catalyst 22. The diesel oxidation catalyst 22 converts carbon-monoxide (CO) and unburned hydrocarbons in the exhaust gases to carbon-dioxide (CO2) and water (H2O). Thereafter, the exhaust gases 38 flow from the diesel oxidation catalyst 22 through the exhaust pipe 30 to the SCR catalyst 24. The SCR catalyst 24 reduces NO and NO2 in the exhaust gases utilizing ammonia (NH3) from the urea-water delivery system 26. Thereafter, the exhaust gases flow from the SCR catalyst 24 through the exhaust pipe 32 to ambient atmosphere.

In this non-limiting example, the system 36 is configured to determine a species concentration, in particular, an NH3 concentration in exhaust gases 38 of the diesel engine 16. Further, the system 36 may be configured to control operation of the diesel engine 16 and of the urea-water delivery system 26. The system 36 includes an electrochemical sensor 50 that may include an NH3 sensor. The system 36 may also include, an air humidity sensor 52, an oxygen sensor 54, and a controller 56 that may include a processor 42 and a memory device 58. Alternatively, the controller 56 may include or be part of an engine control module (ECM) as will be recognized by those in the art. Instead of some of the various sensors shown, the processor 42 may receive water concentration information and/or oxygen concentration information from the ECM. In this example, the electrochemical sensor 50 is operably coupled to the exhaust pipe 32.

Figure 2:
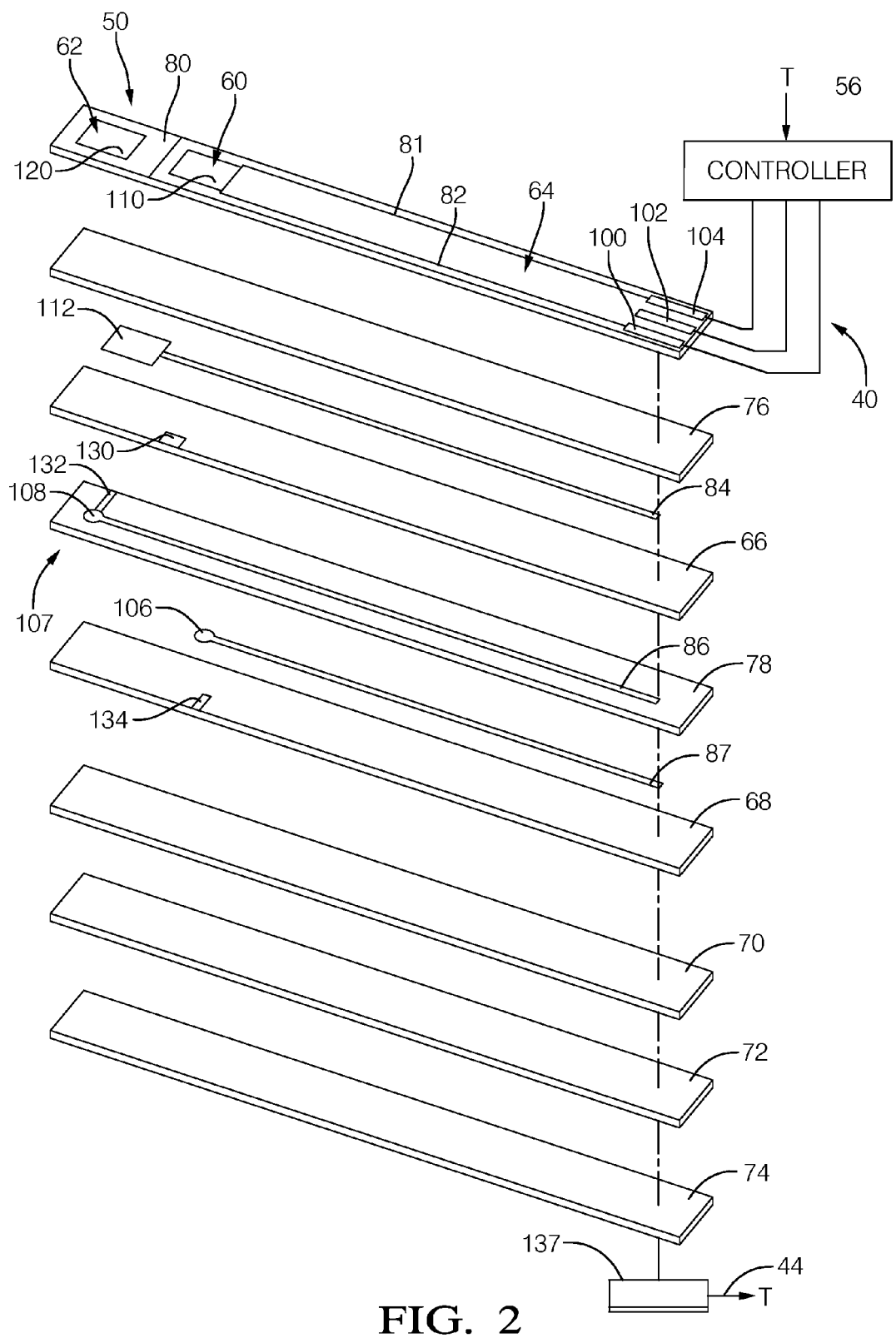
FIG. 2 is an exploded view of an electrochemical sensor suitable for use by the system of FIG. 1 in accordance with one embodiment.

FIG. 2 is a non-limiting example of details of the electrochemical sensor 50. In this example, the electrochemical sensor 50 is configured to output a sensor signal 40 that is indicative of a species concentration (i.e. an NH3 concentration) in the exhaust gases 38. The exhaust gases 38 may include ammonia that was added to the exhaust gases 38 by the urea delivery system 26. It is used to clean the NO and NO2 in the exhaust emitted from the diesel engine 16 as a result of a combustion process. The sensor signal 40 is received by the controller 56. In one exemplary embodiment, the electrochemical sensor 50 is further configured to generate a voltage indicative of an oxides of nitrogen (NO2) concentration in exhaust gases 38 downstream of the diesel oxidation catalyst 22. The electrochemical sensor 50 includes a NO2 sensing cell 60, a NH3 sensing cell 62, insulating layers 64, 66, 68, 70, 72, 74, an electrolyte 76, an active layer 78, a current collector 80, electrical leads 81, 82, 84, 86, 87, contact pads 100,102,104, a temperature sensor 107 formed by the combination of the temperature sensing electrodes 106, 108, an active layer 76 and a contact pad 137. The NH3 sensing cell 62 is provided to generate a voltage indicative of a NH3 concentration in exhaust gases communicating with the NH3 sensing cell 62. The NH3 sensing cell 62 includes a NH3 sensing electrode 120, the reference electrode 112, and the electrolyte 76. The NH3 sensing electrode 120 is disposed on a current collector 80 which is further disposed on the portion of the top surface of the insulating layer 64. The NH3 sensing electrode 120 is electrically coupled via the electrical lead 82 the contact pad 104.

The general function of the NH3 sensing electrode 120 includes NH3 sensing capability (e.g., catalyzing NH3 gas to produce an electromotive force (EMF)), electrical conducting capability (conducting electrical current produced by the EMF), and gas diffusion capability (providing sufficient open porosity so that gas can diffuse throughout the electrode and to the interface region of the NH3 sensing electrode 120 and the electrolyte 76). The NH3 sensing electrode 120 can be constructed from first oxide compounds of vanadium (V), tungsten (W), and molybdenum (Mo), as well as combinations comprising at least one of the foregoing, which can be doped with second oxide components, which can increase the electrical conductivity or enhance the NH3 sensing sensitivity and/or NH3 sensing selectivity to the first oxide components.

Exemplary first components include the ternary vanadate compounds such as bismuth vanadium oxide (BiVO4), copper vanadium oxide (Cu2(VO3)2), ternary oxides of tungsten, and/or ternary molybdenum (MoO3), as well as combinations comprising at least one of the foregoing. Exemplary second component materials include alkali oxides, alkali earth oxides, transition metal oxides, rare earth oxides, and oxides such as SiO2, ZnO, SnO2, PbO, TiO2, In2O3, Ga2O3, Al2O3, GeO2, and Bi2O3, as well as combinations comprising at least one of the foregoing. The NH3 electrode material may also include traditional oxide electrolyte materials such as zirconia, doped zirconia, ceria, doped ceria, or SiO2, Al2O3 and the like, e.g., to form porosity and increase the contact area between the NH3 electrode material and the electrolyte.

The NO2 sensing cell 60 is provided to output a voltage indicative of a NO2, concentration in the exhaust gases 38 communicating with the NO2 sensing cell 60. The NO2 sensing cell 60 includes a NO2 sensing electrode, hereafter referred to as the sense electrode 110, a reference electrode 112, and the electrolyte 76. The sense electrode 110 is disposed on the top surface of the insulating layer 64 and is electrically coupled via the electrical lead 82 to the contact pad 100. The electrolyte 76 is disposed between a bottom surface of the insulating layer 64 and a top surface of the insulating layer 66. The reference electrode 112 is disposed on a top surface of the insulating layer 66, which is disposed adjacent a bottom surface of the electrolyte 76. The reference electrode 112 is electrically coupled via the electrical lead 84 to the contact pad 102. The general function of the sense electrode 110 include, NO2 sensing capability (e.g., catalyzing NO2 gas to produce an EMF), electrical conducting capability (conducting electrical current produced by the EMF), and gas diffusion capability (providing sufficient open porosity so that gas can diffuse throughout the electrode and to the interface region of the electrode and electrolyte).

The sense electrode 110 can be constructed from oxides of ytterbium, chromium, europium, erbium, zinc, neodymium, iron, magnesium, gadolinium, terbium, chromium, as well as combinations comprising at least one of the foregoing, such as YbCrO3, LaCrO3, ErCrO3, EuCrO3, SmCrO3, HoCrO3, GdCrO3, NdCrO3, TbCrO3, ZnFe2O4, MgFe2O4, and ZnCr2O4, as well as combinations comprising at least one of the foregoing. Further, the sense electrode 110 can comprise dopants that enhance the material(s)' NO2 sensitivity and selectivity and electrical conductivity at the operating temperature. These dopants can include one or more of the following elements: Ba (barium), Ti (titanium), Ta (tantalum), K (potassium), Ca (calcium), Sr (strontium), V (vanadium), Ag (silver), Cd (cadmium), Pb (lead), W (tungsten), Sn (tin), Sm (samarium), Eu (europium), Er (Erbium), Mn (manganese), Ni (nickel), Zn (zinc), Na (sodium), Zr (zirconium), Nb (niobium), Co (cobalt), Mg (magnesium), Rh (rhodium), Nd (neodymium), Gd (gadolinium), and Ho (holmium), as well as combinations comprising at least one of the foregoing dopants.

The insulating layer 66 is disposed between the electrolyte 76 and the active layer 78. The insulating layer 66 includes an inlet 130 extending therethrough for communicating exhaust gases to the reference electrode 112. The insulating layer 66 can be constructed from a dielectric material such as alumina.

The active layer 78 is disposed between the insulating layer 66 and the insulating layer 68. The electrode 108 is disposed on the top surface of the active layer 78 and is disposed adjacent an inlet 132 extending through the active layer 78 for communicating exhaust gases to the electrode 108.

The electrode 108 is electrically coupled to an electrical lead 86 which is further electrically coupled to the contact pad 102. The active layer 78 can be constructed from a material such as of which the electrical impedance changes with temperature, such as yttrium doped zirconia, doped ceria, various aluminum-silicates.

The insulating layer 68 is disposed between the active layer 78 and the insulating layer 70. The insulating layer 68 can be constructed from a dielectric material such as alumina. The insulating layer 68 has an inlet 134 extending therethrough for communicating exhaust gases to the electrode 106. The temperature sensing electrodes 106, 108 cooperate with the active layer 78 to form a temperature sensor 107 and are disposed on a top surface and a bottom surface of the active layer 78 and are electrically coupled via the electrical leads 86, 87 to the contact pads 102, 137. The temperature sensor exhibits an electrical impedance (temperature signal T) indicative of a sensor temperature 44 that may correspond to the temperature of the electrochemical sensor 50 that is received by the controller 56. The electrochemical sensor 50 may also include a heater element (not shown) that could be added to influence or control the sensor temperature 44 as will be recognized by those in the art.

The insulating layer 70 is disposed between the insulating layer 68 and the insulating layer 72. The insulating layer 70 can be constructed from a dielectric material such as alumina. The insulating layer 72 is disposed between the insulating layer 70 and the insulating layer 74. The insulating layers 72 and 74 can be constructed from a dielectric material such as alumina.

The contact pads 100, 102, 104 are disposed on the top surface of the insulating layer 64. A voltage between the contact pads 100, 102 is indicative of a NO2 concentration in exhaust gases 38 communicating with the electrochemical sensor 50 and the controller 56. A voltage between the contact pads 104 and 102 is indicative of a NH3 concentration in exhaust gases communicating with the electrochemical sensor 50 and the controller 56.

Referring again to FIG. 1, the air humidity sensor 52 is operably coupled to the air intake manifold 18 of the diesel engine 16. The air humidity sensor 52 is configured to generate a signal that is indicative of humidity level of air inducted into the diesel engine 16, which is received by the controller 56. The oxygen sensor 54 is configured to generate a signal indicative of the concentration of oxygen in the exhaust gases 38. In one exemplary embodiment, the oxygen sensor 54 is operably coupled to the exhaust pipe 28. In another exemplary embodiment, the oxygen sensor 54 is operably coupled to the exhaust pipe 30. In yet another exemplary embodiment, the oxygen sensor 54 is operably coupled to the exhaust pipe 32. In yet another exemplary embodiment, the controller 56 can determine an air-fuel ratio based on a calculated amount of fuel to be delivered to the diesel engine 16, so the signal from the oxygen sensor 54 may not be needed to determine if there was a change in the reference concentration of a reference gas in the exhaust gases 38.

The controller 56 is provided to determine an NH3 concentration in exhaust gases from the diesel engine 16 based on signals from the electrochemical sensor 50, the air humidity sensor 52, and the oxygen sensor 54. Further, the controller 56 is provided to control operation of the diesel engine 16 and of the urea-water delivery system 26. The controller 56 is operably coupled to the electrochemical sensor 50, the air humidity sensor 52, the oxygen sensor 54, and a memory device 58. The memory device 58 is configured to store data and values utilized by the controller 56.

Described above is an electrochemical detection system (the system 36) configured to determine a concentration of a gas in exhaust gases 38 from a combustion process. The reference electrode 112 is in contact with the electrolyte 76. The sense electrode 110 is also in contact with the electrolyte 76 and spaced apart from the reference electrode 112. The electrolyte 76, the reference electrode 112, and the sense electrode 110 cooperate to form an electrochemical sensor (the electrochemical sensor 50) that exposes both the reference electrode 112 and the sense electrode 110 to the exhaust gases 38. The electrochemical sensor 50 is configured to output a sensor signal 40 indicative of a species concentration of a species gas in the exhaust gases. In the example given above, the species gas was nitrogen dioxide (NO2). Alternatively, the sense electrode 110 could be configured to be sensitive to ammonia (NH3), and the NH3 sensing electrode 120 could be configured to be sensitive to some other chemical. It should be recognized that the teachings presented herein are applicable to electrochemical sensors that have only one sensing electrode. That is, it is not a requirement that the electrochemical sensor 50 have two distinct sensing electrodes to determine concentrations of two different species of gas.

Depending on the composition of the electrolyte 76, certain gases are designated a reference gas. For example, if the main charge carrier of the electrolyte 76 is an oxygen ion or proton, any change of gas concentration of oxygen (oxygen ion) or water steam (proton) generally generates a corresponding change in voltage (EMF) at both electrodes. However, it has been has been observed that the sensor signal 40 exhibits a transient error in response to a change in a reference concentration of a reference gas in the exhaust gases.

Figure 3:
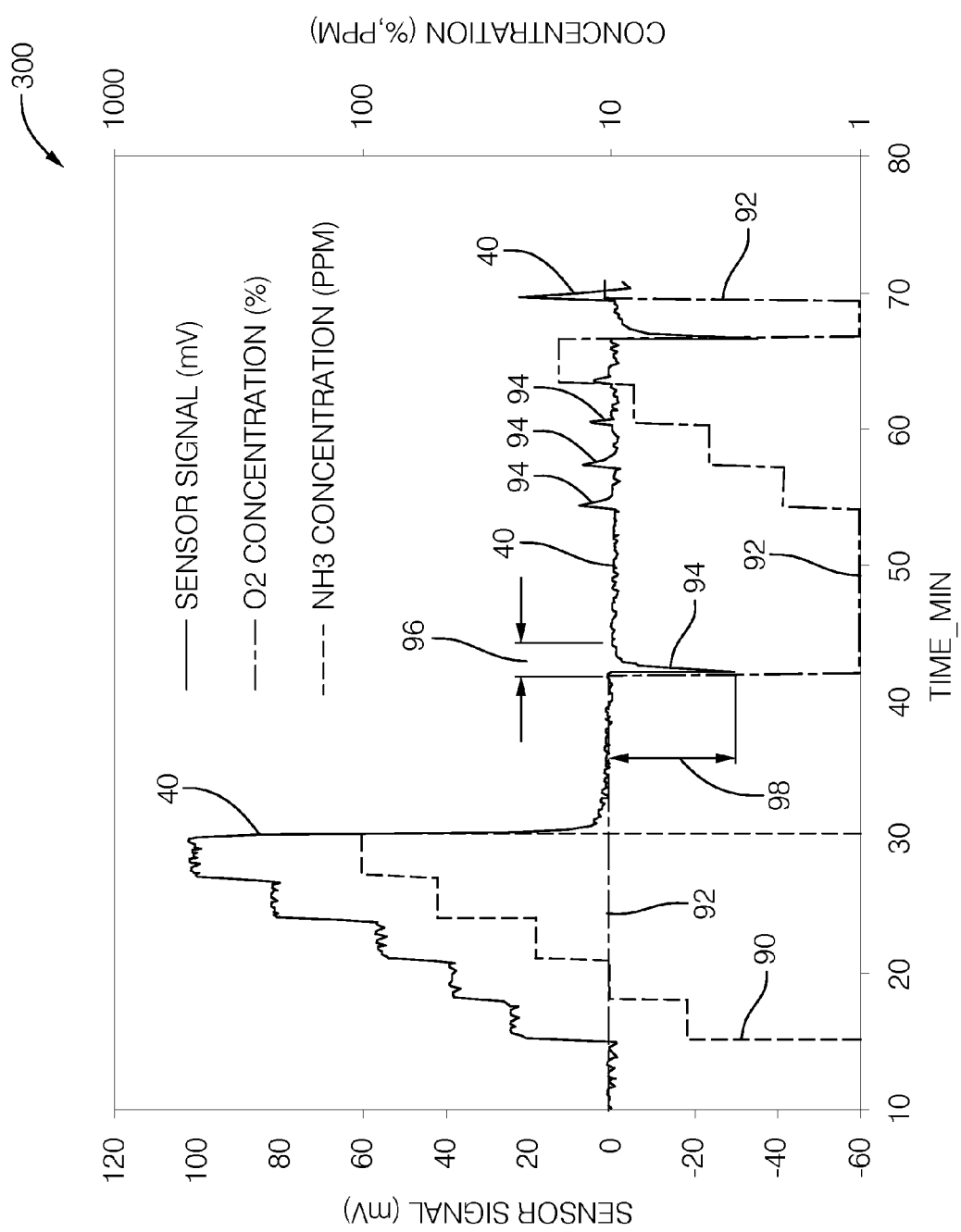
FIG. 3 is a graph of data from a test of the electrochemical sensor of FIG. 2 in accordance with one embodiment.

FIG. 3 is a graph 300 that illustrates a non-limiting example of the sensor signal 40 output by the electrochemical sensor 50 while being exposed to a variable mixture of gases. In this example, the species concentration 90 of the species gas is the concentration of ammonia (NH3), and the reference concentration 92 of the reference gas is the concentration of oxygen (O2). Both concentrations can be read from the right hand vertical log-scale and the unit for ammonia (NH3) is part per million (ppm) in volume and the unit for oxygen is percent (%) by volume. Between the 15-minute mark and the 30-minute mark, the species concentration 90 is varied while the reference concentration 92 is held constant at 10%. As the species concentration 90 is varied, the sensor signal 40 (see left vertical scale in units of mV) varies accordingly to provide an indication of the species concentration 90. At about the 42-minute mark the reference concentration 92 is changed from 10% to 1%, and the species concentration 90 is kept at 0 ppm which cannot be plotted in FIG. 3 as it is outside the plot scale range which is between 1 and 1000 ppm. At about the 54-minute mark the reference concentration 92 is increased in steps. While the electrochemical sensor 50 is preferably configured to vary the sensor signal 40 in response to changes in the species concentration, and be insensitive changes in the reference concentration 92, a transient error 94 is detected when the reference concentration 92 changes at each step change in the reference concentration 92.

While not subscribing to any particular theory, it is believed that this is due to a mismatched oxygen sensing (water steam sensing) response time characteristic. That is, the deliberate difference in materials and/or processing used to apply the sense electrode 110 or the NH3 sensing electrode 120, and the reference electrode 112 causes the two electrodes to have different reference gas response time characteristics. Both electrodes will have exchange charge reaction that involves gas, ions, and electrons between each electrode and the electrolyte 76 where electrons come from the electrodes, and ions come from the electrolyte 76, or from the reference gas and the electrons. If both electrodes are exposed to the same gas atmosphere and have mismatched response times to the reference concentration 92, a transient change to the sensor signal 40 (the transient error 94) will be generated whenever there is change of the reference concentration 92 in the gas atmosphere. For example, if the main charge carrier of the solid electrolyte is oxygen ion or proton, any change of gas concentration of oxygen (oxygen ion) or water steam (proton) would generate a change to the sensor signal 40 if both electrodes have mismatched oxygen sensing (water steam sensing) response time characteristics. By way of example and not limitation, the well-known Nernst equation may be used to estimate the error duration 96 and/or error magnitude 98 of the transient error 94 given different response time characteristics of the sense electrode 110 or the NH3 sensing electrode 120, and the reference electrode 112.

To prevent the transient error 94 from causing the controller 56 to make an incorrect adjustment to the engine control signal 46, or the urea delivery system control signal, or other devices operated by the controller 56, a processor 42 may be provided and configured to determine the species concentration 90 based on the sensor signal 40, and to determine an estimate of the transient error 94 based on an operating condition of the combustion process. As used herein, and will be explained in more detail below, the operating condition of the combustion process may be determined, influenced or indicated by any operating characteristic such as exhaust gas recirculation level, engine load, flue opening size, fuel pressure, fuel rate, inlet air pressure, inlet air flow rate, and the like that can cause a change in the reference concentration 92. This information can be available to processor 42 from an engine control module or ECM (not shown). By way of further example and not limitation, if the diesel engine 16 is suddenly decelerated, the exhaust gases 38 may have a sudden but possibly temporary, increase in the concentration of oxygen in the exhaust gases 38, i.e. an increase in the reference concentration 92. Alternatively, other sensors may provide direct information instead of the information provided by the engine control module ECM. For example the oxygen sensor 54, may be used to detect a change in the reference concentration 92. As such, an estimate of the transient error 94 may be made based on a signal from the oxygen sensor 54. In general, the objective of estimating the transient error is to general data that corresponds to or accurately predicts the actual transient error 94 that varies the value of the sensor signal 40.

The processor 42 may include or be a microprocessor or other control circuitry such as analog and/or digital control circuitry including an application specific integrated circuit (ASIC) for processing data as should be evident to those in the art. The processor 42 may include memory, including non-volatile memory, such as electrically erasable programmable read-only memory (EEPROM) for storing one or more routines, thresholds and captured data. The one or more routines may be executed by the processor 42 to perform steps for processing signals received by the processor 42 as described herein.

In one embodiment, the processor 42 may be configured to compensate the sensor signal 40 received by the processor 42 based on the estimate of the transient error 94. For example, if the fuel injectors of the diesel engine 16 are suddenly turned off because the vehicle 10 is coasting and the inlet air flow rate is known, a change in the reference concentration 92 can be predicted, and so an estimate of the transient error 94 can be predicted. The response to a change in the reference concentration 92 by the electrochemical sensor 50 can be estimated by a formula or by a look-up table that was developed by empirical testing of the electrochemical sensor 50. By way of further explanation and not limitation, the magnitude an duration of the transient error 94 shown at the 42-minute mark on FIG. 3 corresponds to the change in the reference concentration 92 shown on the graph. If a change in the operating condition of the diesel engine 16 is expected to cause a similar change in the reference concentration 92, then the transient error 94 can be predicated or estimated, and compensated for by adjusting or compensating the sensor signal 40 accordingly.

If the system 36 includes the oxygen sensor 54, then changes of oxygen concentration in the exhaust gases 38 can be directly measured, and the effect on the sensor signal 40 can be readily predicted or estimated, and compensated for.

In another embodiment, the processor 42 may be configured to ignore the sensor signal 40 for an error duration 96 if an error magnitude 98 of the estimate of the transient error is greater than an error threshold, for example 5 mV. Such an approach may be advantageous to reduce the empirical testing expense necessary to compensate the sensor signal 40 as proposed above. This approach may be especially suitable for applications where changes in the operating conditions are relatively infrequent and so rapid adjustments to, for example, the urea-water delivery system 26 are not necessary to keep emissions low.

It is recognized that the transient response characteristics of the sense electrode 110, the NH3 sensing electrode, and the reference electrode 112 may vary with temperature. As such, if the electrochemical sensor 50 is configured to the sensor temperature 44, then the processor 42 may be further configured to determine the estimate of the transient error based on the sensor temperature. For example, if the sensor temperature is relatively high (e.g. after the diesel engine has been running for an hour at a high engine load), then the response time characteristics are generally faster than when the sensor temperature 44 is relatively low (e.g. at engine start or after idling for more than fifteen minutes). In accordance with the embodiments describe above, the processor 42 may be further configured to compensate the sensor signal 40 received by the processor 42 based on the transient error 94 and the sensor temperature 44, or the processor 42 may be further configured to ignore the sensor signal 40 for an error duration 96 if the error magnitude 98 of the transient error 94 is greater than an error threshold, where the error duration 96 is determined based on the sensor temperature 44.

If the electrochemical sensor 50 is equipped with a heater element (not shown) then the processor 42 may be further configured to operate the heater element to control the sensor temperature 44, and thereby make the transient errors more predictable as the sensor temperature 44 will not be solely at the mercy of the temperature of the exhaust gases 38.

Figure 4:
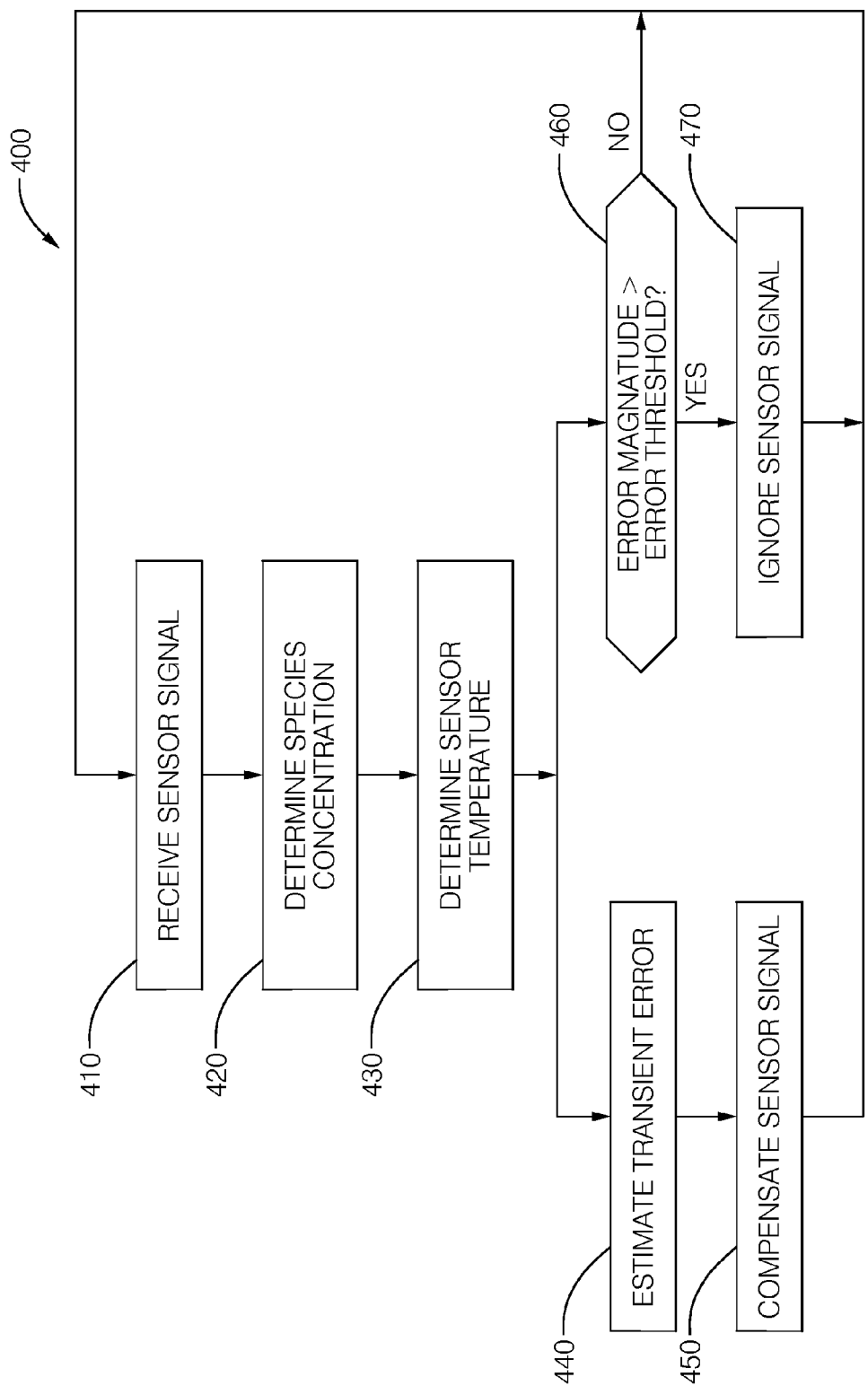
FIG. 4 is a flow chart of a method executed by the system of FIG. 1 in accordance with one embodiment.

FIG. 4 illustrates a non-limiting example of a method 400 to determine a concentration of a gas in exhaust gases 38 from a combustion process such as the operation of a diesel engine 16.

Step 410, RECEIVE SENSOR SIGNAL, may include receiving a sensor signal from an electrochemical sensor, wherein the sensor is configured to expose both a reference electrode and a sense electrode of the sensor to the exhaust gases, wherein the sensor signal is indicative of a species concentration of a species gas in the exhaust gases, wherein the sensor signal exhibits a transient error in response to a change in a reference concentration of a reference gas in the exhaust gases Step 420, DETERMINE SPECIES CONCENTRATION, may include determining the species concentration 90 based on the sensor signal 40 by, for example, using a value of the sensor signal 40 to look-up a corresponding species concentration on a look-up table.

Step 430, DETERMINE SENSOR TEMPERATURE, is an optional step that may be executed if the electrochemical sensor 50 is equipped with the temperature sensor 107, and may include the processor 42 receiving a sensor temperature 44 from the electrochemical sensor 50.

Step 440, ESTIMATE TRANSIENT ERROR, may include determining or estimating an estimate of the transient error based on an operating condition of the combustion process such as a change in the rate of fuel or the air-to-fuel ratio being delivered to the diesel engine 16, or based on a signal from an oxygen sensor or an air-to-fuel ration sensor. The estimate of the transient error may consider the sensor temperature 44 if available. The estimate may be in the form of a series of data corresponding to the shape of the transient error 94 illustrated in FIG. 3, or it may be an error duration 96 of the processor 42 is configured to ignore the sensor signal 40 as a way to prevent the transient error 94 from undesirably affecting operation of the vehicle 10 or emissions produced by the operation of the diesel engine 16.

FIG. 4 illustrates the logic paths to steps 440 and 460 as being parallel, thereby suggesting that the alternatives are mutually exclusive. However, it is contemplated that these steps may be organized series-wise so that both are executed based on, for example, the present operating condition of the diesel engine. For example, if the diesel engine has just been started so the oxygen sensor 54 is relatively cold and may not accurately indicate the reference concentration (i.e. the concentration of oxygen), an alternative method may execute step 440 if the diesel engine 16 is warmed-up, and execute step 460 if the diesel engine 16 is relatively cold.

Step 450, COMPENSATE SENSOR SIGNAL, may include compensating the sensor signal received based on the estimate of the transient error. For example, if the estimate of the transient error is a series of data that is thought to match the actual transient error, that data may be combined with the sensor signal 40 received by the processor 42 in a manner effective to negate the transient error 94.

Step 460, ERROR MAGNITUDE>ERROR THRESHOLD?, may include comparing the magnitude of the estimated transient error (the error magnitude 98) to a predetermined threshold, 5 mV for example. Alternatively, if the oxygen sensor 54 is available and the oxygen sensor indicates a change in the reference concentration 92 that is greater than some threshold, 10% for example, then that may serve as a way to determine if the YES or NO logic path should be taken from step 460. If NO, the method 400 return's to step 410. If YES, the method proceeds to step 470.

Step 470, IGNORE SENSOR SIGNAL, may include ignoring the sensor signal 40 for an error duration 96 if an error magnitude 98 of the estimate of the transient error is greater than an error threshold.

Accordingly, a system 36, a controller 56 for the system 36 and a method 400 of operating the system 36 is provided. If the oxygen concentration time profile and the knowledge of oxygen sensing response time of sense electrode 110 or the NH3 sensing electrode 120 and the reference electrode 112 are known, the error in the sensor signal 40 caused by changes in oxygen changes can be predicted and corrected. The correction may be done either by ignoring the sensor signal, or correcting (compensating) the sensor signal 40. The teaching presented herein can be applied to other gas sensing cells and are not limited to ammonia sensing cell as presented by the examples shown herein.

While this invention has been described in terms of the preferred embodiments thereof, it is not intended to be so limited, but rather only to the extent set forth in the claims that follow.

We claim:

1. A method to determine a concentration of a gas in exhaust gases of a combustion process, said method comprising:
   receiving a sensor signal from an electrochemical sensor, wherein the electrochemical sensor is configured to expose both a reference electrode and a sense electrode of the electrochemical sensor to the exhaust gases such that the sense electrode is in contact with an electrolyte and the sense electrode is spaced apart from the reference electrode, wherein the sensor signal is indicative of a species concentration of a species gas in the exhaust gases, wherein the sensor signal exhibits a transient error in response to a change in a reference concentration of a reference gas in the exhaust gases;
   determining the species concentration based on the sensor signal; and
   estimating the transient error based on an operating condition of the combustion process.

2. The method in accordance with claim 1, wherein the method further comprises
   compensating the sensor signal received based on the estimate of the transient error.

3. A method to determine a concentration of a gas in exhaust gases of a combustion process, said method comprising:
   receiving a sensor signal from an electrochemical sensor, wherein the electrochemical sensor is configured to expose both a reference electrode and a sense electrode of the electrochemical sensor to the exhaust gases such that the sense electrode is in contact with an electrolyte and the sense electrode is spaced apart from the reference electrode, wherein the sensor signal is indicative of a species concentration of a species gas in the exhaust gases, wherein the sensor signal exhibits a transient error in response to a change in a reference concentration of a reference gas in the exhaust gases;
   determining the species concentration based on the sensor signal;
   estimating the transient error based on an operating condition of the combustion process; and
   ignoring the sensor signal for an error duration if an error magnitude of the estimate of the transient error is greater than an error threshold.

4. The method in accordance with claim 1, wherein the method further comprises
   receiving a sensor temperature, wherein the step of estimating of the transient error is also based on the sensor temperature.

5. The method in accordance with claim 4, wherein the method further comprises compensating the sensor signal based on the transient error and the sensor temperature.

6. A method to determine a concentration of a gas in exhaust gases of a combustion process, said method comprising:
receiving a sensor signal from an electrochemical sensor, wherein the electrochemical sensor is configured to expose both a reference electrode and a sense electrode of the electrochemical sensor to the exhaust gases such that the sense electrode is in contact with an electrolyte and the sense electrode is spaced apart from the reference electrode, wherein the sensor signal is indicative of a species concentration of a species gas in the exhaust gases, wherein the sensor signal exhibits a transient error in response to a change in a reference concentration of a reference gas in the exhaust gases;
determining the species concentration based on the sensor signal;
estimating the transient error based on an operating condition of the combustion process;
receiving a sensor temperature, wherein the step of estimating of the transient error is also based on the sensor temperature; and
ignoring the sensor signal for an error duration if an error magnitude of the transient error is greater than an error threshold, wherein the error duration is determined based on the sensor temperature.

* * * * *